United States Patent
Barone et al.

(10) Patent No.: US 7,041,278 B2
(45) Date of Patent: May 9, 2006

(54) COSMETIC COMPOSITIONS WITH IMPROVED THERMAL STABILITY AND WEAR

(75) Inventors: Salvatore J. Barone, Staten Island, NY (US); Ellen M. McGarvey, Bayonne, NJ (US); Louis J. Veltry, Hopatcong, NJ (US)

(73) Assignee: COTY Inc, Morris Plains, NJ (US)

( * ) Notice: Subject to any disclaimer, the term of this patent is extended or adjusted under 35 U.S.C. 154(b) by 0 days.

(21) Appl. No.: 10/210,397

(22) Filed: Jul. 31, 2002

(65) Prior Publication Data

US 2004/0028641 A1    Feb. 12, 2004

(51) Int. Cl.
*A61Q 1/06*    (2006.01)
*A61Q 1/08*    (2006.01)

(52) U.S. Cl. ............................ 424/64; 424/63; 424/69; 424/401

(58) Field of Classification Search ................... 424/63, 424/64, 401
See application file for complete search history.

(56) References Cited

U.S. PATENT DOCUMENTS

| | | | |
|---|---|---|---|
| 4,389,418 A | 6/1983 | Burton | |
| 5,538,718 A | 7/1996 | Aul et al. | |
| 5,773,611 A * | 6/1998 | Zysman et al. | 424/401 |
| 5,871,756 A | 2/1999 | Jeffcoat et al. | |
| 5,968,530 A | 10/1999 | Arquette | |
| 5,997,889 A | 12/1999 | Durr et al. | |
| 6,159,454 A | 12/2000 | Schuhmacher et al. | |
| 6,207,714 B1 | 3/2001 | Clouatre et al. | |
| 6,231,873 B1 | 5/2001 | Noda et al. | |
| 6,254,876 B1 | 7/2001 | de la Poterie et al. | |
| 6,277,358 B1 | 8/2001 | Calello et al. | |
| 6,280,746 B1 | 8/2001 | Arquette et al. | |
| 6,315,990 B1 | 11/2001 | Farer et al. | |
| 6,350,459 B1 | 2/2002 | Suzuki et al. | |
| 6,403,112 B1 | 6/2002 | Motitschke et al. | |
| 6,407,142 B1 | 6/2002 | Courbriere et al. | |
| 6,409,995 B1 | 6/2002 | Habeck et al. | |
| 6,409,997 B1 | 6/2002 | Castro | |
| 6,413,526 B1 | 7/2002 | Bazin et al. | |
| 6,416,573 B1 | 7/2002 | Horino et al. | |
| 6,416,751 B1 | 7/2002 | Roulier et al. | |
| 6,416,760 B1 | 7/2002 | Breton et al. | |
| 6,416,773 B1 | 7/2002 | Heidenfelder et al. | |
| 6,649,177 B1 * | 11/2003 | Howard et al. | 424/401 |

OTHER PUBLICATIONS

Barone, S. J., et al., "Lipstick Technology," Monograph No. 8, Society of Cosmetic Chemists (2002).

* cited by examiner

*Primary Examiner*—Jyothsna Venkat
(74) *Attorney, Agent, or Firm*—Madeline F. Baer; Heidi Reese; Brown Raysman Millstein Felder and Steiner LLP

(57) ABSTRACT

Anhydrous cosmetic compositions comprising hydrolyzed jojoba ester with increased short- and long-term thermal stability are disclosed. The compositions exhibit increased thermal stability of at least about 1° C., preferably at least about 5° C., and most preferably, at least about 10° C., and optimally at least about 15° C. The compositions provide excellent aesthetic and long-wear properties and are resistant to liquid syneresis and are useful in cosmetic and personal care formulations.

22 Claims, No Drawings

COSMETIC COMPOSITIONS WITH IMPROVED THERMAL STABILITY AND WEAR

FIELD OF THE INVENTION

This invention relates to cosmetic compositions; and more particularly, anhydrous cosmetic compositions containing hydrolyzed jojoba ester.

BACKGROUND OF THE INVENTION

It is well known that stabilizers are necessary ingredients in cosmetic formulations. For example, without adequate stabilizers, lipsticks are prone to creeping and melting. While some effort has been spent in identifying improved fundamental materials such as emulsion stabilizers (see, e.g., U.S. Pat. No. 5,871,756), most of the effort in cosmetic stability improvement has been directed toward transfer- and wear-resistance enhancements. U.S. Pat. No. 6,227,358, for example, describes a lipstick composition in which film-forming polymers cross-link after application to the lips to form a semi-permanent, transfer- and wear-resistant film. There has also been a substantial amount of work in which small particles are added to formulations to improve transfer- and wear-resistance. One such formulation, described in U.S. Pat. No. 6,315,990, uses fluorosilane-coated pigment or filler particles to improve wear resistance and waterproofing properties of a variety of cosmetic compositions. Similarly, U.S. Pat. No. 6,254,876 discloses the use of a dispersion of surface-stabilized polymer particles to produce water-, wear- and transfer-resistant cosmetic compositions.

One of the drawbacks of many conventional cosmetic formulations that has not been adequately addressed is the susceptibility to melting at high temperatures. Because of this susceptibility, it is necessary for consumers to protect cosmetic products, especially lipsticks, from exposure to the high temperatures that can be reached, for example, in an enclosed car or in direct sunlight. Conventional approaches to increasing the melting point of lipsticks generally involve producing formulations with a greater proportion of high-melting waxes. Unfortunately, lipsticks with high wax contents have an aesthetically undesirable harsh feel when applied to the lips.

Jojoba is a common ingredient in cosmetics, and because of its emollient properties, is often used in skin lotions, shampoos and hair conditioners (see, e.g., the websites of Crabtree and Evelyn, Ltd. (Woodstock, Conn.) and Nature's Gate Natural Health and Beauty Products (Chatsworth, Calif.) U.S. Pat. Nos. 5,968,530 and 6,280,746 describe jojoba ester-based compositions that serve as emollient additives for a variety of pigment-containing cosmetic products. Barone, et al., in "Lipstick Technology," Monograph Number 8, Society of Cosmetic Chemists (2002) also disclose the use of jojoba esters as lipstick additives that provide superior emolliency, improved stick structure, and are oxidatively stable. Jojoba, a natural product derived from the jojoba tree, comprises a mixture of long-chained linear esters with a combination of mixed tocopherols, free sterols and other unsaponifiable material making up the balance. Jojoba esters exhibit stability at high temperatures, and as such, are known additions to cosmetic compositions to increase thermostability. See e.g., "Cosmetic Chemistry of Natural Jojoba" available from the website of Purcell Jojoba International (Avila Beach, Calif.), and U.S. Pat. No. 5,538,718, describing a cosmetic stick composition in which jojoba, or one of a variety of other naturally regenerable vegetable waxes and oils, is substituted for conventional high-melting paraffin waxes. Jojoba esters are also able to resist hydrolysis and oxidation and thus have become a common replacement for conventional lipids such as triglyceride oils in cosmetic compositions. Jojoba esters thus offer cosmetic chemists a natural cosmetic lipid with excellent emolliency, moisturization and oxidative stability. Cosmetic compositions containing jojoba esters, however, are prone to melting and sweating at high temperatures.

Accordingly, there is a need in the industry for heat-resistant cosmetic compositions that are oxidatively stable and that have a pleasant aesthetic quality when applied to the skin.

SUMMARY OF THE INVENTION

In accordance with the present invention, anhydrous cosmetic compositions comprising a hydrolyzed jojoba ester with increased thermal stability are provided. The compositions of the present invention exhibit increased thermal stability in comparison to conventional anhydrous cosmetics, without sacrificing any aesthetic emollient properties or product breakage. The compositions maintain thermal stability with increases in temperature of at least about 1° C., preferably at least about 5° C., most preferably, at least about 10° C., and optimally, at least about 15° C. in comparison to conventional anhydrous cosmetics. For example, conventional anhydrous cosmetics typically exhibit liquid syneresis above about 61° C. The compositions of the present invention, however, are able to withstand liquid syneresis and breakage when subject to increases in temperature as described above. In addition to stability after short-term exposure to increased temperature, the compositions of the present invention afford thermal stability after long-term heat exposure, making them particularly suitable for long distance transport and storage.

Advantageously, the compositions of the present invention need only include the hydrolyzed ester component in a small amount in order to exhibit increased thermal stability. By way of example, the beneficial properties associated with the present invention are provided when about 1.0% of the hydrolyzed ester is added to the composition in addition to conventional components or substituted for another conventional carrier, such a solidifying agent or a wax. In accordance with the present invention, thermal stability is increased as the quantity of hydrolyzed jojoba ester added to the composition increases. In a preferred embodiment, the composition comprises 5.0%, and more preferably, 20.0% of the ester component.

Another embodiment of the invention provides an anhydrous cosmetic composition comprising from about 0.01% to about 80% by weight of a cosmetic active; and from about 20% to about 80% by weight of a carrier comprising hydrolyzed jojoba ester in an amount sufficient to increase the thermal stability of the composition. As above, these compositions maintain thermal stability when exposed to increased temperatures of at least about 1° C., preferably at least about 5° C., most preferably, at least about 1° C., and optimally, at least about 15° C. In addition, thermal stability is achieved with as little as about a 1.0% addition of the hydrolyzed jojoba ester, and increases as the amount of the ester is increased in the composition.

The compositions of the present invention can be formulated for a number of different cosmetic uses including, but not limited to, lipstick, eye shadow, eye liner, foundation, concealer and blush. The compositions also find use in personal care formulations such as, but not limited to, antiperspirants, sunscreens, hair care products and the like.

DETAILED DESCRIPTION OF THE INVENTION

The present invention is directed to anhydrous cosmetic compositions containing a hydrolyzed jojoba ester that imparts desirable emollient and oxidative stability properties as well as a thermal stability. Advantageously, the compositions can withstand high temperatures without melting or sweating. "Anhydrous," as used herein, refers to compositions containing less than about 5 wt. % of free or added water. "Melting," as used herein, refers to the phase change from a solid to a liquid. This phase change is characterized by a melting point, occurring at a specific temperature or range of temperatures, at which solid and liquid phases coexist in equilibrium. Melting point may be determined with any standard melting point apparatus known in the art, such as, e.g., a Fisher-Johns melting point apparatus or a Thomas Hoover melting point apparatus. "Sweating," as used herein, refers to the phenomenon of liquid syneresis. Liquid syneresis occurs when liquid is expelled from a gel network as a result of structural changes to the network. "Thermal stability" refers to the ability to resist liquid syneresis and product breakdown as temperatures are increased at least 1° C. above conventional cosmetic composition melting points. For example, a hard stick composition with thermal stability does not exhibit liquid syneresis and maintains a breakage value of at least about 1.2 pounds/square inch when exposed to at least about 5° C., preferably at least about 10° C., and most preferably, at least about a 15° C. increase in temperature over the temperature at which conventional cosmetics exhibit such characteristics, typically at about 61° C. or above. Hydrolyzed jojoba ester refers to a straight chain monomer of esterified alcohols and acids which has been subject to hydrolysis.

Jojoba is a naturally occurring plant lipid comprising a mixture of unbranched long-chain esters. It is an excellent cosmetic ingredient due to its natural origin and its desirable emolliency, moisturization and rapid absorption, and properties. Jojoba is an extremely safe substance, causing no adverse effects upon long-term use, and is compatible with the vast majority of conventional cosmetic ingredients. In addition, its natural lack of support for microbial growth, and its oxidative stability decreases the need for the preservatives and masking agents that are required in cosmetic compositions utilizing other plant-derived or synthetic lipids. Surprisingly, it has been found that hydrolyzed jojoba ester increases thermal stability in cosmetic compositions over conventional jojoba esters.

The compositions of the invention contain a hydrolyzed jojoba ester having a saponification value ranging from about 0.050% to about 15.0%. The saponification value is a measure of the mean molecular weight of the component fatty acids. It is related to the molar mass of the fat, and is defined as the number of milligrams of potassium hydroxide required to saponify 1 g of oil or fat, i.e., to neutralize the free fatty acids and the fatty acids combined as acylglycerols. It is determined by measuring the amount of excess potassium hydroxide remaining after the fatty acids are boiled under reflux with an excess of ethanolic potassium hydroxide solution and back-titrated with standard hydrochloric acid solution. The saponification value can also be determined by calculation, using the fatty acid composition of the sample determined by gas chromatography. This calculation may be applied to all normal oils and fats, provided they contain only low concentrations of free fatty acids, monoglycerides and diglycerides. (see, e.g., the website of Lipid Analysis Unit at the Scottish Crop Research Institute (Invergowrie, Dundee, Scotland). Unsaponifiable matter refers to substances that are resistant to saponification by strong alkali, e.g., potassium hydroxide.

Hydrolyzed jojoba ester may be purchased under the trade name of Floraesters K-100, from International Flora Technologies, Ltd. (Gilbert, Ariz.).

Surprisingly, hydrolyzed jojoba ester does not have a determinable melting point. Accordingly, the addition of a hydrolyzed jojoba ester to an anhydrous cosmetic composition, or alternatively, the substitution of the ester for all or a part of another component of the composition, results in a composition having a greater thermal stability than compositions without a hydrolyzed ester component. Advantageously, thermal stability is maintained under increased temperature conditions by adding a sufficient quantity, e.g., about 1.0% by weight of hydrolyzed jojoba ester, for another carrier component in an anhydrous cosmetic composition. By way of example, addition of 5% hydrolyzed jojoba ester can increase the thermal stability of a cosmetic composition as much as 110° C. This increase in thermal stability becomes even more dramatic as additional hydrolyzed jojoba ester is added to the composition; for example, cosmetic compositions with a 20% hydrolyzed jojoba ester component, demonstrate as much as a 15° C. increase in thermal stability.

In addition to an increase in thermal stability, cosmetic compositions prepared in accordance with the present invention exhibit desirable aesthetic application properties. These properties include smooth and non-greasy sensations during and after application of the composition to the skin, and highly emollient properties after application. Prior to the discovery that compositions comprising a hydrolyzed jojoba ester component exhibit an increase in thermal stability, the thermal stability of typical cosmetic compositions could only be raised by increasing the total wax content of the composition, thereby imparting an unpleasant harsh feel to the product upon application to the skin.

The hydrolyzed jojoba ester used in the present invention requires both heat and friction to melt. Accordingly, the present invention provides a composition having a significantly higher melting point than conventional anhydrous cosmetics. Without intending to be bound by theory, it is thought that the friction caused during application to the body will be sufficient to melt the composition enough to allow it to spread easily across the skin. Since the melting point of the composition is significantly higher than skin temperature (approximately 37° C.), after application the composition will reform on the skin and stay in place, and thus provide longer wear properties than conventional anhydrous cosmetics.

In addition to an increased thermal stability to short term exposure to high temperatures, the compositions of the present invention also exhibit excellent stability to long-term heat exposure. As previously discussed, one measure of thermal stability is the absence of sweating or liquid syneresis of the cosmetic composition. Another common measure of stability is the degree of breakage exhibited by the composition. "Breakage" or "product breakage" measures the resistance of a cosmetic composition to a force, which is perpendicular to the vertical axis of the composition. Breakage is measured in stick compositions by a Chatillon Digital Force Gauge (Ametek, Inc., Paoli, Pa.), and in softer anhydrous compositions by a penetromoter, (Koehler Instrument Company, Inc., Bohemia, N.Y.), an instrument that measures the consistency of a semiliquid or semisolid material by measuring the penetration depth to which a specified cone or needle under a given force falls into the material as defined by ASTM D217-97.

Cosmetic compositions in accordance with the present invention can be formulated as hard sticks, soft solids, creams or other product forms having similar breakage values. Exemplary breakage values are at least about 1.2 pounds/square inch force, and typically range from about 1.2 pounds/square inch to 8.5 pounds/square inch force. Hard stick compositions will preferably have a breakage value of at least about 1.2 pounds/square inch force to about 2.4 pounds/square inch force, and more preferably, at least about 1.8 pounds/square inch force. For softer compositions, such as creams or soft solids, the composition preferably exhibits a penetration value of at least about 0.15 to about 15.0 pounds/square inch force, more preferably about 0.5 to about 5.0 pounds/square inch force, and optimally about 1.2 to about 2.4 pounds/square inch force.

In accordance with the present invention, anhydrous cosmetic compositions can be exposed to temperatures as high as 45° C. (a temperature often found inside a hot car) for up to several weeks without the occurrence of liquid syneresis or a breakage. The compositions of the present invention thus exhibit superior aesthetic qualities (including ease of application), even after heat exposure.

The cosmetic compositions of the present invention comprise from about 0.01% to about 70%, preferably from about 10% to about 65%, and most preferably from about 30% to about 60% by weight of a cosmetic active. Suitable actives include any cosmetic active that is compatible with the essential ingredients of the present invention. Exemplary cosmetic actives include moisturizers, emollients, fillers, colorants, perfumes or fragrances, skin conditioners, vitamins, photoprotectants (e.g., sunscreens), antiperspirants, antioxidants, anti-wrinkle materials, as well as any other materials suitable for topical applications. Anhydrous cosmetic compositions in accordance with the present invention include, but are not limited to, lipsticks, eye shadows, eye liners, foundations, concealers and blushes, as well as personal care products, such as antiperspirants, hair care products, sunscreens, and analgesic compositions, and may be prepared in stick, cake, or cream form.

Suitable cosmetic actives for use in accordance with the present invention include, but are not limited to those disclosed in U.S. Pat. Nos. 6,416,760; 6,350,459; 6,231,873; 6,207,174; 6,416,773; 6,416,751; 6,413,526; 6,159,454; 6,407,142; 6,409,995; 5,997,889; 4,389,418; 6,416,751; 6,403,112; 6,416,573; and 6,409,997.

The cosmetic compositions of the present invention further comprise from about 20% to about 80%, preferably from about 30% to about 75%, and most preferably from about 40% to about 70% by weight of a carrier. As used herein, "carrier" refers to solidifying agents and/or oils. The choice of solidifying agent and oil for use in the compositions of the invention will depend upon the type of composition (e.g., lipstick, foundation, blush, antiperspirant, sunscreen) and the desired breakage, and is well within the skill level of a routine practitioner. A carrier may have secondary functions, as for example, as a cosmetic active.

Exemplary solidifying agents comprise fats and waxes. Suitable fats are triesters of glycerin and predominantly $C_8$–$C_{18}$ fatty acids. Animals fats such as lard and tallow may be used, but vegetable fats such as cocoa butter and solidifying vegetable oils such as hydrogenated castor, coconut and palm kernel oils are preferable. Synthetic triglycerides such as glyceryl tristearate, glyceryl tripalmitate and glyceryl triacetyl hydroxystearate are well suited to the cosmetic compositions of the present invention. Lipsticks, for example, generally comprise fat as the solidifying agent in quantities less than about 15% by weight.

Suitable waxes for use in the compositions of the present invention include animal, vegetable, mineral, and synthetic waxes. Lanolin ($C_{18}$–$C_{26}$ alcohol esters, fatty acids, cholesterol and terpenols and acetylated derivatives thereof) and beeswax are both useful where an animal wax component is desired. Carnauba and candelilla wax, either singly or in combination; and ozokerite and ceresin, naturally-occurring, petroleum-derived microcrystalline waxes, as well as other hydrocarbon waxes such as paraffin wax, are suitable vegetable and mineral wax components, respectively. Synthetic waxes, such as Performalene (New Phase Technologies, Sugar Land, Tex.) and Siltel (Baker Petrolite Corporation, Sugar Land, Tex.) as well as organosilane and organofluro waxes such as Siliconyl Beeswax, Siliconyl Candelilla and Siliconyl Synthetic Paraffin Wax (Koster Keunen, Inc., Watertown, Conn.) are useful components of the present invention. Other suitable synthetic waxes include alkyl methyl siloxane, such as AMS wax (Dow Corning, Midland, Mich.), and alkyl dimethicone wax (GE Silicone SF1642, GE Silicone, Waterford, N.Y.), and synthetic fluoro waxes such as fluoro hexacosonate (Koester Keunen, Inc., Watertown, Conn.).

Suitable oils include vegetable oils such as coconut and palm kernel oil and preferably, castor oil, mineral oils, and synthetic oils such as branched chain alcohols such as isocetyl and isosteryl alcohol and esters such as capric/caprylic triglyceride and octyl hydroxystearate, and silicone fluids such as dimethicone, organosilicone oils such as phenyl trimethicone, and perfluropolyethers such as Fomblin® (Edison S.p.A., Milan, Italy). An excellent discussion of suitable carriers for use in the present invention can be found in Barone et al. "Lipstick Technology," Monograph, Number 8, Society of Cosmetic Chemists (1992).

In accordance with the present invention, hydrolyzed jojoba ester may be added as a part of the carrier component during formulation of the cosmetic compositions or, alternatively, it may be substituted for all or a part of another carrier component. In either instance, at least about 1.0%, preferably at least about 5% and more preferably, at least about 20% impart the beneficial features associated with the cosmetic compositions of the present invention.

The cosmetic compositions of the present invention may further comprise any additional optional materials that are known for use in cosmetic or personal care products, or which are otherwise suitable for topical application. Such optional materials include, but are not limited to, disbursing agents, masking agents, preservatives, processing agents, additives having specific physicochemical properties, such as polymeric film formers and the like.

The cosmetic compositions of the present invention may be prepared by any known or otherwise effective technique suitable to provide a composition having the characteristics described herein.

The following examples are presented to more clearly illustrate the invention, and should not be construed as limiting the scope of the invention in any way.

EXAMPLES

Example 1

This example demonstrates that thermal stability is increased in a lipstick prepared with a 5% by weight addition of hydrolyzed jojoba ester:

|  | Wt. % | | | | | | |
| --- | --- | --- | --- | --- | --- | --- | --- |
| Material | Run 1 (control) | Run 2 | Run 3 | Run 4 | Run 5 | Run 6 | Run 7 |
| Oils & Waxes: | | | | | | | |
| Polyethylene | 7.70 | 7.70 | 7.70 | 7.70 | 7.70 | 7.70 | 7.70 |
| Ceresin | 4.85 | 4.85 | 4.85 | 4.85 | 4.85 | 4.85 | 4.85 |
| Polyglyceryl-3 Beeswax | 6.17 | 6.17 | 6.17 | 6.17 | 6.17 | 6.17 | 6.17 |
| PVP/Hexadecene Copolymer | 2.50 | 2.50 | 2.50 | 2.50 | 2.50 | 2.50 | 2.50 |
| Lecithin/C12-16 Alcohols/Stearic Acid/Palmitic Acid | 2.00 | 2.00 | 2.00 | 2.00 | 2.00 | 2.00 | 2.00 |
| Sorbitan Sesquioleate | 1.50 | 1.50 | 1.50 | 1.50 | 1.50 | 1.50 | 1.50 |
| Tocopherol | 0.20 | 0.20 | 0.20 | 0.20 | 0.20 | 0.20 | 0.20 |
| Oleyl Alcohol | 7.50 | 7.50 | 7.50 | 7.50 | 7.50 | 7.50 | 7.50 |
| Propylparaben | 0.20 | 0.20 | 0.20 | 0.20 | 0.20 | 0.20 | 0.20 |
| Jojoba Esters | 15.50 | 10.50 | 10.50 | 10.50 | 10.50 | 10.50 | 10.50 |
| Hydrolyzed Jojoba Esters (lot A) | — | 5.00 | — | — | — | — | — |
| (lot B) | — | — | 5.00 | — | — | — | — |
| (lot C) | — | — | — | 5.00 | — | — | — |
| (lot D) | — | — | — | — | 5.00 | — | — |
| (lot E) | — | — | — | — | — | 5.00 | — |
| (lot F) | — | — | — | — | — | — | 5.00 |
| Triisostearin | 8.00 | 8.00 | 8.00 | 8.00 | 8.00 | 8.00 | 8.00 |
| Squalane | 4.00 | 4.00 | 4.00 | 4.00 | 4.00 | 4.00 | 4.00 |
| Isoeicosane | 2.00 | 2.00 | 2.00 | 2.00 | 2.00 | 2.00 | 2.00 |
| Ethylhexyl Palmitate | 4.48 | 4.48 | 4.48 | 4.48 | 4.48 | 4.48 | 4.48 |
| Colorants, Filler and Oil: | | | | | | | |
| Pigment in Castor Oil | 22.29 | 22.29 | 22.29 | 22.29 | 22.29 | 22.29 | 22.29 |
| Silica | 2.50 | 2.50 | 2.50 | 2.50 | 2.50 | 2.50 | 2.50 |
| Quantum Specific: | | | | | | | |
| Castor Oil | 3.00 | 3.00 | 3.00 | 3.00 | 3.00 | 3.00 | 3.00 |
| Mica | 2.01 | 2.01 | 2.01 | 2.01 | 2.01 | 2.01 | 2.01 |
| Sodium Polyaspartate/Water | 0.10 | 0.10 | 0.10 | 0.10 | 0.10 | 0.10 | 0.10 |
| Vegetal Fill Spheres | 3.00 | 3.00 | 3.00 | 3.00 | 3.00 | 3.00 | 3.00 |
| Fragrance: | | | | | | | |
| Fragrance | 0.50 | 0.50 | 0.50 | 0.50 | 0.50 | 0.50 | 0.50 |
|  | 100.00 | 100.00 | 100.00 | 100.00 | 100.00 | 100.00 | 100.00 |

The oils, waxes and preservatives were heated to 85–90° C. and mixed for 15–20 minutes to ensure uniformity. Color grinds were added and mixed for 20 minutes, after which the shade was examined and matched to a standard. After the shade was properly matched (and the quantum specific maintained), optional ingredients and fragrance were added and the composition drop batched.

Melting point and breakage data for these lipsticks was as follows:

|  | Run 1 (control) | Run 2 | Run 3 | Run 4 | Run 5 | Run 6 | Run 7 |
| --- | --- | --- | --- | --- | --- | --- | --- |
| Melting Point (° C.) | 61.0 | 71.0 | 72.3 | 70.4 | 69.9 | 70.0 | 63.4 |
| Breakage (lbs/in$^2$) | 2.10 | 2.23 | 1.96 | 2.10 | 2.26 | 2.07 | 1.96 |

The data shows that for 6 out of 7 runs, lipsticks formulated in accordance with the invention have significantly increased melting points in comparison with a control lipstick of similar composition. Breakage values were maintained, despite an increased melting point.

Example 2

This experiment confirms the results obtained in Example 1. Lipsticks were prepared according to the following formulation and in accordance with the method of Example 1:

|  | Wt. % | | |
| --- | --- | --- | --- |
| Material | Run 1 | Run 2 | Run 3 |
| Polyethylene | 7.70 | 7.70 | 7.70 |
| Ceresin | 4.85 | 4.85 | 4.85 |
| Polyglyceryl-3 Beeswax | 6.17 | 6.17 | 6.17 |
| PVP/Hexadecene Copolymer | 2.50 | 2.50 | 2.50 |
| Lecithin/C12-16 Alcohols/Stearic Acid/Palmitic Acid | 2.00 | 2.00 | 2.00 |
| Sorbitan Sesquioleate | 1.50 | 1.50 | 1.50 |
| Tocopherol | 0.20 | 0.20 | 0.20 |
| Oleyl Alcohol | 7.50 | 7.50 | 7.50 |
| Propylparaben | 0.20 | 0.20 | 0.20 |
| Jojoba Esters | 10.50 | 10.50 | 10.50 |
| Hydrolyzed Jojoba Esters | 5.00 | — | — |
| (lot A) | | | |
| (lot B) | — | 5.00 | — |
| (lot C) | — | — | 5.00 |
| Triisostearin | 8.00 | 8.00 | 8.00 |
| Squalane | 4.00 | 4.00 | 4.00 |
| Isoeicosane | 2.00 | 2.00 | 2.00 |
| Ethylhexyl Palmitate | 4.48 | 4.48 | 4.48 |
| Methicone/Silica | 2.50 | 2.50 | 2.50 |
| Pigment in Castor Oil | 28.45 | 28.95 | 28.45 |
| Mica | 1.85 | 1.85 | 1.85 |
| Sodium Polyaspartate/Water | 0.10 | 0.10 | 0.10 |
| Fragrance | 0.50 | 0.0 | 0.50 |
|  | 100.00 | 100.00 | 100.00 |

Melting point and breakage data for these lipsticks were as follows:

|  | Control | Run 1 | Run 2 | Run 3 |
| --- | --- | --- | --- | --- |
| Melting Point (° C.) | 63.0 | 69.5 | 71.0 | 71.8 |
| Breakage (lbs/in$^2$) | 1.82 | 2.10 | 2.02 | 2.22 |

For all three experimental runs, lipsticks formulated in accordance with the invention have significantly increased melting points in comparison with a control lipstick of similar composition. Breakage values were maintained, despite an increased melting point.

Example 3

The example demonstrates the increase in melting point associated with lipsticks prepared with about a 20% by weight addition of hydrolyzed jojoba ester. This example further illustrates that hydrolyzed jojoba ester can be substituted for other solidifying agents or waxes:

| Material | Wt. % |
| --- | --- |
| Hydrolyzed Jojoba Esters | 19.4 |
| Sorbitan Olivate | 3.9 |
| Polyethylene | 6.2 |
| Polyglyceryl-3 Beeswax | 7.8 |
| Oleyl Alcohol | 14.5 |
| Lecithin | 0.5 |
| Octyl Decanol | 8.7 |
| Castor Oil | 14.5 |
| Pigment in Castor Oil | 21.8 |
| Silica | 1.2 |
| Mica | 1.5 |
|  | 100.00 |

The lipsticks were prepared according to the method of Example 1. The lipstick prepared according to this formulation exhibited a melting point of 76° C. as determined by a Fisher-Johns melting point apparatus, and a melting point range of 68–73° C. as measured by a Thomas Hoover melting point apparatus.

Example 4

This example demonstrates that compositions of the present invention maintain thermal stability after long-term exposure to elevated temperatures. Lipsticks were prepared as in Example 1:

| | Run 1: | | | | | | | | | | | |
| --- | --- | --- | --- | --- | --- | --- | --- | --- | --- | --- | --- | --- |
| | .25 hr | .5 hr | 1 hr | 24 hr | 48. hr | 1 wk | 2 wks | 3 wks | 4 wks | 5 wks | 6 wks | 7 wks | 8 wks |
| 25° C. | 4 | 4 | 4 | 4 | 4 | 4 | 3 | 3 | 3 | matte surface with small pimpling | | |
| 37° C. | 4 | 4 | 4 | 4 | 4 | 4 | 4 | 4 | 4 | 3 | 3 | 3 | 3 |
| 45° C. | 4 | 4 | 4 | 4 | 4 | 3 | 3 | rough surface | | | | |

| | Run 2: | | | | | | | | | | | |
|---|---|---|---|---|---|---|---|---|---|---|---|---|
| | .25 hr | .5 hr | 1 hr | 24 hr | 48 hr | 1 wk | 2 wks | 3 wks | 4 wks | 5 wks | 6 wks | 7 wks | 8 wks |
| 25° C. | 4 | 4 | 4 | 3 | 3 | 3 | rough surface | | | | | | |
| 37° C. | 4 | 4 | 4 | 4 | 4 | 4 | 4 | 3 | 3 | 3 | 3 | 3 | 3 |
| 45° C. | 4 | 4 | 4 | 3 | 3 | 3 | 3 | rough surface | | | | | |

4 = excellent stability
3 = very good stability

The lipsticks were subjected to 8 weeks of exposure to elevated temperatures. Samples from each run were held at 25° C. (room temperature) as a control, at 37° C. (skin temperature), and at 45° C. (simulating, for example, the temperature inside a hot car). Control lipsticks showed signs of pimpling after two weeks. As can be seen, lipsticks formulated according to the present invention have excellent stability to long-term heat exposure, and therefore superior stability when compared to control lipsticks.

Example 5

An anhydrous cosmetic foundation is prepared by heating the oils and waxes until a temperature of 85–90° C. is reached and the mixture is of uniform consistency. The colorants, fillers and oils are added under agitation for approximately 20 minutes until a uniform color is attained and a suitable quantum specific value attained. Optional ingredients and fragrance are added and the composition is formed as desired.

| Material | Wt. % |
|---|---|
| Oils & Waxes: | |
| Ozokerite Wax | 8.060 |
| Ethylhexyl Palmitate | 36.050 |
| Microcrystalline Wax | 2.100 |
| Sorbitan Sesquioleate | 0.500 |
| Hydrolyzed Jojoba Ester | 5.000 |
| Colorants, Filler & Oil: | |
| Polymethyl Methacrylate | 12.900 |
| Mica | 4.500 |
| Talc | 3.574 |
| Titanium Dioxide | 20.500 |
| Black Iron Oxide | 0.352 |
| Red Iron Oxide | 0.592 |
| Yellow Iron Oxide | 2.672 |
| Quantum Specific: | |
| Silica | 2.100 |
| Optional Ingredients: | |
| Preservatives | 1.000 |
| Fragrance: | |
| Fragrance | 0.100 |

An increase in thermal stability is observed over a control sample without a hydrolyzed jojoba ester component.

Example 6

A lipstick is prepared in accordance with the formulation and the procedure of Example 1. A panel of 35 women are given the control lipstick; a second panel of 35 women are given the lipstick containing 5% hydrolyzed jojoba ester. Lipstick feel and wear is observed at 2, 4, 6 and 8-hour intervals after application. In all instances, the panel provided with the 5% hydrolyzed jojoba ester composition reported superior aesthetic quality (emolliency, smoothness, and non-greasy feeling) over the control panel. In addition, the lipstick containing 5% hydrolyzed jojoba ester exhibited longer wear characteristics (staying power on lips) than the control.

Example 7

This example demonstrates that the melting point of a lipstick is increased 1° C. with a 1% by weight addition of hydrolyzed jojoba ester. Lipsticks were prepared according to the following formulation and in accordance with the method of Example 1:

| | Wt. % | |
|---|---|---|
| Material | Run 1 (Control) | Run 2 |
| Polyethylene | 7.70 | 7.70 |
| Ceresin | 4.85 | 4.85 |
| Polyglyceryl —3 Beeswax | 6.17 | 6.17 |
| PVP/Hexadecene Copolymer | 2.50 | 2.50 |
| Lecithin/C12-16 Alcohols/Stearic Acid/Palmitic Acid/Behenyl Alcohol/Glyceryl Stearate | 2.00 | 2.00 |
| Sorbitan Sesquioleate | 1.50 | 1.50 |
| Tocopherol | 0.20 | 0.20 |
| Oleyl Alcohol | 7.50 | 7.50 |
| Propylparaben | 0.20 | 0.20 |
| Jojoba Esters | 15.50 | 14.50 |
| Hydrolyzed Jojoba Esters | — | 1.00 |
| Triisostearin | 8.00 | 8.00 |
| Squalane | 4.00 | 4.00 |
| Isoeicosane | 2.00 | 2.00 |
| Ethylhexyl Palmitate | 4.48 | 4.48 |
| Silica/Methicone | 2.50 | 2.50 |
| Pigment/Castor Oil | 28.45 | 28.45 |
| Mica | 1.85 | 1.85 |
| Sodium Polyaspartate/Water | 0.10 | 0.10 |
| Fragrance | 0.50 | 0.50 |
| | 100.00 | 100.00 |

The melting points for these lipsticks, as determined with a Thomas Hoover melting point apparatus, are as follows:

| | Run1 (Control) | Run2 |
|---|---|---|
| Melting Point (° C.) | 63 | 64 |

What is claimed is:

1. An anhydrous cosmetic composition comprising a cosmetic active and a sufficient quantity of hydrolyzed jojoba ester necessary to maintain thermal stability in the anhydrous composition subject to about a 1° C. or higher increase in temperature.

2. The composition of claim 1, wherein the composition comprises at least about 1.0% by weight of hydrolyzed jojoba ester.

3. The composition of claim 1, wherein the composition comprises at least about 5% by weight of hydrolyzed jojoba ester.

4. The composition of claim 1, wherein the composition comprises at least about 20% by weight of hydrolyzed jojoba ester.

5. The composition of claim 1, wherein the composition can maintain thermal stability when subject to about a 5° C. or higher increase in temperature.

6. The composition of claim 1, wherein the composition can maintain thermal stability when subject to about a 10° C. or higher increase in temperature.

7. The composition of claim 1, wherein the composition can maintain thermal stability when subject to about a 15° C. or higher increase in temperature.

8. The composition of claim 1, wherein the composition is a lipstick.

9. An anhydrous cosmetic composition comprising:
   (a) from about 0.01% to about 70% by weight of a cosmetic active; and
   (b) from about 20% to about 80% by weight of a carrier, the carrier comprising hydrolyzed jojoba ester in an amount sufficient to maintain thermal stability in an anhydrous composition subject to about a 1° C. or higher increase in temperature.

10. The composition of claim 9, wherein the cosmetic active is present in an amount of from about 10% to about 65%.

11. The composition of claim 9, wherein the cosmetic active is present in an amount of from about 30% to about 60%.

12. The composition of claim 9, wherein the carrier is present in an amount of from about 30% to about 75%.

13. The composition of claim 9, wherein the carrier is present in an amount of from about 40% to about 70%.

14. The composition of claim 9, wherein the composition comprises at least about 1% by weight of hydrolyzed jojoba ester.

15. The composition of claim 9, wherein the composition comprises at least about 5% by weight of hydrolyzed jojoba ester.

16. The composition of claim 9, wherein the composition comprises at least about 10% by weight of hydrolyzed jojoba ester.

17. The composition of claim 9, wherein the composition comprises at least about 20% by weight of hydrolyzed jojoba ester.

18. The composition of claim 9, wherein the composition can maintain thermal stability when subject to about a 5° C. or higher increase in temperature.

19. The composition of claim 9, wherein the composition can maintain thermal stability when subject to about a 10° C. or higher increase in temperature.

20. The composition of claim 9, wherein the composition can maintain thermal stability when subject to about a 15° C. or higher increase in temperature.

21. The composition of claim 9, wherein the composition is a lipstick.

22. An anhydrous cosmetic composition comprising hydrolyzed jojoba ester in an amount sufficient to increase the thermal stability and wear of the anhydrous composition.

* * * * *